| United States Patent [19] | [11] Patent Number: 4,579,869 |
| Cragoe, Jr. et al. | [45] Date of Patent: Apr. 1, 1986 |

[54] SUBSTITUTED [(2,3-DIHYDRO-1-OXO-1H-INDEN-5-YL)AMINO]ALKANOIC ACIDS, THEIR DERIVATIVES AND THEIR SALTS

[75] Inventors: Edward J. Cragoe, Jr., Lansdale; Otto W. Woltersdorf, Jr., Chalfont, both of Pa.

[73] Assignee: Merck & Co., Inc., Rahway, N.J.

[21] Appl. No.: 761,949

[22] Filed: Aug. 2, 1985

[51] Int. Cl.$^4$ .................. C07C 101/78; A61K 31/195
[52] U.S. Cl. ...................... 514/561; 560/43; 562/456; 562/457; 514/534
[58] Field of Search ............ 560/43; 562/456, 457; 514/534, 561

[56] References Cited

U.S. PATENT DOCUMENTS

| 3,954,852 | 5/1976 | Shen et al. | 562/457 |
| 4,081,554 | 3/1978 | Cragoe et al. | 514/569 |
| 4,096,267 | 6/1978 | Cragoe et al. | 514/569 |
| 4,148,916 | 4/1979 | Payne | 562/457 |
| 4,249,021 | 2/1981 | Cragoe et al. | 562/457 |

*Primary Examiner*—James H. Reamer
*Attorney, Agent, or Firm*—Charles M. Caruso; Daniel T. Szura; Hesna J. Pfeiffer

[57] ABSTRACT

The invention relates to novel substituted [(2,3-dihydro-1-oxo-1H-inden-5-yl)amino]alkanoic acids, their derivatives and their salts. The compounds are useful for the treatment and prevention of injury to the brain and of edema due to head trauma, stroke (particularly ischemic), arrested breathing, cardiac arrest, Reye's syndrome, cerebral thrombosis, cerebral embolism, cerebral hemorrhage, cerebral tumors, encephalomyelitis, spinal cord injury, hydrocephalus, post-operative brain injury trauma, edema due to cerebral infections and various brain concussions.

12 Claims, No Drawings

SUBSTITUTED [(2,3-DIHYDRO-1-OXO-1H-INDEN-5-YL)AMINO]ALKANOIC ACIDS, THEIR DERIVATIVES AND THEIR SALTS

BACKGROUND OF THE INVENTION

Trauma to the brain or spinal cord caused by physical forces acting on the skull or spinal column, by ischemic stroke, arrested breathing, cardiac arrest, Reye's syndrome, cerebral thrombosis, cerebral embolism, cerebral hemorrhage, encephalomyelitis, hydrocephalus, post-operative brain injury, cerebral infections and various concussions results in edema and swelling of the affected tissues. This is followed by ischemia, hypoxia, necrosis, temporary or permanent brain and/or spinal cord injury and may result in death. The tissue mainly affected are classified as grey matter, more specifically astroglial cells. The specific therapy currently used for the treatment of the medical problems described include various kinds of diuretics (particularly osmotic diuretics), steroids (such as, 6-α-methylprednisolone succinate) and barbiturates. The usefulness of these agents is questionable and they are associated with a variety of untoward complications and side effects. Thus, the compounds of this invention comprise a novel and specific treatment of medical problems where no specific therapy is available.

A recent publication entitled "Agents for the Treatment of Brain Injury" 1. (Aryloxy)alkanoic Acids, Cragoe et al., J. Med. Chem., (1982) 25, 567–79, reports on recent experimental testing of agents for treatment of brain injury and reviews the current status of treatment of brain injury.

Some compounds having structures related to the compounds of the present invention have been reported to be diuretic and saluretic agents in Cragoe U.S. Pat. Nos. 4,070,539 and 4,249,021. Additionally, Williams, H. W. R. et al., J. Org. Chem., 44, 4060 (1979) reported that the ether linkage in [(6,7-dichloro-1-oxo-5-indanyl)oxy]acetic acids could be substituted by nitrogen under strongly basic conditions. There is, however, no suggestion in the patents or publication that any of the compounds disclosed therein would be of use in the treatment of brain injury.

The compounds of the invention have the added advantage of being devoid of the pharmacodynamic, toxic or various side effects characteristic of the diuretics, steroids and barbiturates.

DESCRIPTION OF THE INVENTION

The compounds of the instant invention are best characterized by reference to the following structural Formula (I):

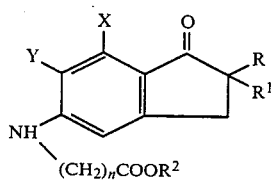

Wherein R is lower alkyl, branched or unbranched, containing from 1 to 5 carbon atoms such as methyl, ethyl, n-propyl, isopropyl and the like, aryl such as phenyl, halo substituted aryl such as p-fluorophenyl or p-chlorophenyl, aralkyl such as benzyl, cycloalkyl containing from 3 to 6 nuclear carbon atoms such as cyclopropyl, cyclobutyl, cyclopentyl and the like, or cycloalkyl-lower alkyl containing from 4 to 7 total carbon atoms such as cyclopentylmethyl and the like. $R^1$ is hydrogen or lower alkyl. $R^2$ is hydrogen, lower alkyl or lower alkyl-amino-lower-alkyl such as 2-(dimethylamino)ethyl. X and Y are halo or lower alkyl, and n is 1 to 4.

When the R and $R^1$ substituents are different, the 2-position carbon atom of the indane ring is asymmetric and these compounds of the invention are racemic. However, these compounds or their precursors can be resolved so that the pure enantiomers can be prepared, thus the invention includes the pure enantiomers. This is an important point since some of the racemates consist of one enantiomer which is much more active than the other one. Furthermore, the less active enantiomer generally possesses the same intrinsic toxicity as the more active enantiomer. In addition, it can be demonstrated that the less active enantiomer depresses the inhibitory action of the active enantiomer at the tissue level. Thus, for three reasons it is advantageous to use the pure, more active enantiomer rather than the racemate.

Since the products of the invention are acidic, the invention also includes the obvious pharmaceutically acceptable salts, such as the sodium, potassium, ammonium, trimethylammonium, piperazinium, 1-methylpiperazinium, guanidinium, bis-(2-hydroxethyl)ammonium, N-methylglucosammonium and the like salts.

It is also to be noted that the compounds of Formula I, as well as their salts, often form solvates with the solvents in which they are prepared or from which they are recrystallized. These solvates may be used per se or they may be desolvated by heating (e.g. at 70° C.) in vacuo.

Although the invention primarily involves novel substituted [(2,3-dihydro-1-oxo-1H-inden-5-yl)amino]alkanoic acids, and their salts, it also includes their derivatives, such as esters, amides, oximes, hydrazones and the like. Additionally, this invention includes pharmaceutical compositions in unit dosage form containing a pharmaceutical carrier and an effective amount of a compound of Formula I, its (−) or (+) enantiomer, or the pharmaceutically acceptable salts thereof, for treating brain injury. The method of treating a person with brain injury by administering said compounds or said pharmaceutical compositions is also a part of this invention.

PREFERRED EMBODIMENT OF THE INVENTION

The preferred embodiments of the instant invention are realized in structural Formula II

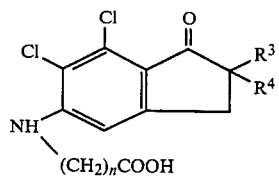

$R^3$ is aryl, such as phenyl, halo substituted aryl, such as p-fluorophenyl or p-chlorophenyl, or cycloalkyl containing from 3 to 6 nuclear carbon atoms such as cyclopropyl, cyclobutyl, cyclopentyl and the like; $R^4$ is lower alkyl containing from 1 to 5 carbon atoms; n is 1 to 4.

Also included are the enantiomers of each racemate.

Preferred compounds are [(6,7-dichloro-2-cyclopentyl-2,3-dihydro-2-methyl-1-oxo-1H-inden-5-yl)amino]acetic acid and its (—)-enantiomer and their salts.

Especially preferred are the pure enantiomers since, in most instances, one enantiomer is more active biologically then its antipode.

Included within the scope of this invention are the pharmaceutically acceptable salts of substituted [(2,3-dihydro-1-oxo-1H-inden-5-yl)amino]alkanoic acids, since a major medical use of these compounds is solutions of their soluble salts which can be administered parenterally.

Thus, the acid addition salts can be prepared by the reaction of the substituted [(2,3-dihydro1-oxo-1H-inden-5-yl)amino]alkanoic acids of this invention with an appropriate amine, ammonium hydroxide, guanidine, alkali metal hydroxide, alkali metal carbonate, alkali metal bicarbonate, quaternary ammonium hydroxide and the like. The salts selected are derived from among the non-toxic, pharmaceutically acceptable bases.

The synthesis of the substituted [(2,3-dihydro-1-oxo-1H-inden-5-yl)amino]alkanoic acids of Formula I are generally carried out by the following route illustrated by the preparation of [(6,7-dichloro-2-cyclopentyl-2,3-dihydro-2-methyl-1-oxo-1H-inden-5-yl)amino]acetic acid.

The starting material 2,3-dichloro-2-cyclopentyl-2,3-dihydro-5-hydroxy-2-methyl-1H-inden-1-one is alkylated with ethylene bromide in the presence of potassium carbonate to form 5(2-bromoethoxy)-6,7-dichloro-2-cyclopentyl-2,3-dihydro-2-methyl-1H-inden-1-one (Step 1). This material is then reacted with liquid ammonia to accomplish the substitution of bromine by ammonia and to form 6,7-dichloro-2-cyclopentyl-2,3-dihydro-5-(2-aminoethoxy)-2-methyl-1H-inden-1-one (Step 2). Following the formation of the compound of Step 2, an intramolecular Smiles rearrangement takes place (Step 3). The 6,7-dichloro-2-cyclopentyl-2,3-dihydro-5-(2-hydroxyethylamino)2-methyl-1H-inden-1-one formed in Step 3 is then oxidized with Jones Reagent ($CrO_3$, $H_2SO_4$, $H_2O$) to form 5-amino-6,7-dichloro-2-cyclopentyl2,3-dihydro-2-methyl-1H-inden-1-one (Step 4). When n is 1, 3 or 4, alkylation of the amino group (Step 5) with a haloalkanoic acid ester, such as ethyl bromoacetate, followed by acid or base hydrolysis of the alkyl ester (Step 6) gives a compound of the present invention, such as [6,7-dichloro-2-cyclopentyl-2,3-dihydro-2-methyl-1-oxo-1H-inden-5-yl)amino]acetic acid. When n is 3, alkylation with 4-bromo-1-butene followed by oxidation with potassium permanganate gives the compound of the present invention, without the need for hydrolysis. The starting material used in these examples is obtained as shown in Woltersdorf, O. W. et al., J. Med. Chem., 20, 1400 (1977). This synthetic route is illustrated

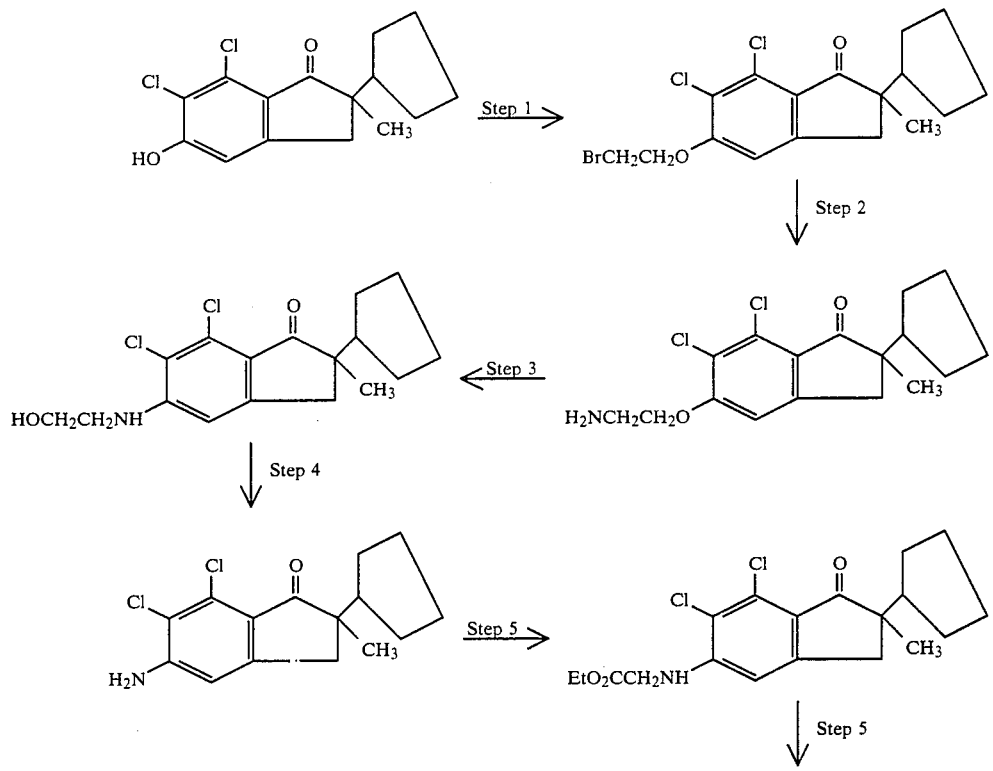

-continued

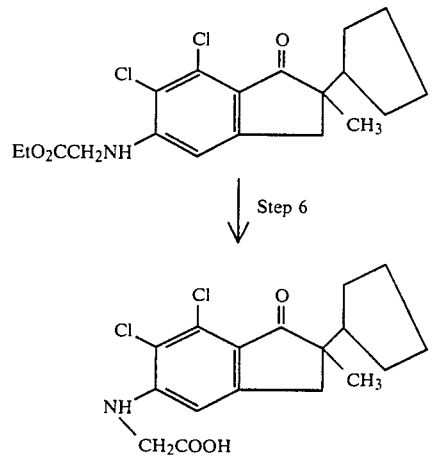

Those compounds possessing an asymmetric carbon atom at the 2-position of the indane ring consist of a racemate composed of two enantiomers. The resolution of the two enantiomers may by accomplished by forming a salt of the racemic mixture with an optically active base such as (+) or (−)amphetamine, (−)cinchonidine, dehydroabietylamine, (+) or (−)-α-methylbenzylamine, (+) or (−)(1-naphthyl)ethylamine (+) cinchonine, brucine, or strychnine and the like in a suitable solvent such as methanol, ethanol, 2-propanol, benzene, acetonitrile, nitromethane, acetone and the like. There is formed in the solution, two diastereomeric salts, one of which is usually less soluble in the solvent than the other. Repetitive recrystallization of the crystalline salt generally affords a pure diastereomeric salt from which is obtained the desired pure enantiomer. The optically pure enantiomer of the compound of Formula I is obtained by acidification of the salt with a mineral acid, isolation by filtration and recrystallization of the optically pure antipode.

The other optically pure antipode may generally be obtained by using a different base to form the diastereomeric salt. It is of advantage to isolate the partially resolved acid from the filtrates of the purification of the first diastereomeric salt and to further purify this substance through the use of another optically active base. It is especially advantageous to use an optically active base for the isolation of the second enantiomer which is the antipode of the base used for the isolation of the first enantiomer. For example, if (+)-α-methylbenzylamine was used first, then (−)-α-methylbenzylamine is used for the isolation of the second (remaining) enantiomer.

The acid addition salts are prepared by reacting the acids of Formula I with an appropriate base, for example, alkali metal or alkaline earth bicarbonate, carbonate or alkoxide, an amine, ammonia, an organic quaternary ammonium hydroxide, guanidine and the like.

The reaction is generally conducted in water when alkali metal hydroxides are used, but when alkoxides and the organic bases are used, the reaction may be conducted in an organic solvent, such as ether, ethanol, dimethylformamide and the like.

The preferred salts are the pharmaceutically acceptable salts such as sodium, potassium, ammonium and the like.

Inasmuch as there are a variety of symptoms and severity associated with grey matter edema, particularly when it is caused by head trauma, stroke, cerebral hemorrhage or embolism, post-operative brain surgery trauma, spinal cord injury, cerebral infections and various brain concussions, the precise treatment is left to the practioner. Generally, candidates for treatment will be indicated by the results of the patient's initial general neurological status, findings on specific clinical brain stem functions and findings on computerized axial tomography (CAT), nuclear magnetic resonance (NMR) or positron emission tomography (PET) scans of the brain. The sum of the neurological evaluation is presented in the Glascow Coma Score or similar scoring system. Such a scoring system is often valuable in selecting the patients who are candidates for therapy of this kind.

The compounds of this invention can be administered by a variety of established methods, including intravenously, intramuscularly, subcutaneously, or orally. The parenteral route, particularly the intravenous route of administration, is preferred, especially for the very ill and comatose patient. Another advantage of the intravenous route of administration is the speed with which therapeutic brain levels of the drug are achieved. It is of paramount importance in brain injury of the type described to initiate therapy as rapidly as possible and to maintain it through the critical time periods. For this purpose, the intravenous administration of drugs of the type of Formula I in the form of their salts is superior.

A recommended dosage range for treatment is expected to be from 0.05 mg/kg to 50 mg/kg of body weight as a single dose, preferably from 0.5 mg/kg to 20 mg/kg. An alternative to the single dose schedule is to administer a primary loading dose followed by a sustaining dose of half to equal the primary dose, every 4 to 24 hours. When this multiple dose schedule is used the dosage range may be higher than that of the single dose method. Another alternative is to administer an ascending dose sequence of an initial dose followed by a sustaining dose of 1½ to 2 times the initial dose every 4 to 24 hours. For example, 3 intravenous doses of 8, 12 and 16 mg/kg of body weight can be given at 6 hour intervals. If necessary, 4 additional doses of 16 mg/kg of body weight can be given at 12 hour intervals. Another effective dose regimen consists of a continuous intravenous infusion of from 0.05 mg/kg/hr to 3.0 mg/kg/hr. Of course, other dosing schedules and amounts are possible.

One aspect of this invention is the treatment of persons with grey matter edema by concomitant administration of a compound of Formula I or its salts, and an antiinflammatory steroid. These steroids are of some, albeit limited, use in control of white matter edema associated with ischemic stroke and head injury. Steroid therapy is given according to established practice as a supplement to the compound of Formula I as taught elsewhere herein. Similarly, a barbiturate may be administered as a supplement to treatment with a compound of Formula I.

The compounds of Formula I are utilized by formulating them in a pharmaceutical composition such as tablet, capsule or elixir for oral administration. Sterile solutions or suspensions can be used for parenteral administration. A compound or mixture of compounds of Formula I, or its physiologically acceptable salt, is compounded with a physiologically acceptable vehicle, carrier, excipient, binder, preservative, stabilizer, flavor, etc. in a dosage form as called for by accepted pharmaceutical practice.

Illustrative of the adjuvants which may be incorporated in tablets, capsules and the like are the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, lactose, or saccharin; a flavoring agent such as peppermint, oil of wintergreen or cherry. When the dosage unit form is a capsule, it may contain in addition to materials of the above type a liquid carrier such as a fatty oil. Various other materials may be present as coatings or to otherwise enhance the pharmaceutical elegance of the preparation. For instance, tablets may be coated with shellac, sugar or the like. A syrup or elixir may contain the active compound, sucrose as a sweetening agent, methyl and propyl parabens as preservatives, a dye and a flavoring such as cherry or orange flavor.

Sterile compositions for injection or infusion can be formulated according to conventional pharmaceutical practice by dissolving the active substance in a conventional vehicle such as water, saline or dextrose solution by forming a soluble salt in water using an appropriate base, such as a pharmaceutically acceptable alkali metal hydroxide, alkali metal bicarbonate, ammonia, amine or guanidine. Alternatively, a suspension of the active substance in a naturally occurring vegetable oil like sesame oil, coconut oil, peanut oil, cottonseed oil, etc., or a synthetic fatty vehicle like ethyl oleate or the like may be formulated for injection or infusion. Buffer, preservatives, antioxidants and the like can be incorporated as required.

The basic premise for the development of agents for the treatment of brain injury of the types described is based on the studies in experimental head injury by R. S. Bourke et al. (R. S. Bourke, M. A. Daze and H.K. Kimelberg, Monograph of the International Glial Cell symposium, Leige, Bel. Aug. 29-31, 1977 and references cited therein) and experimental stroke by J. H. Garcia et al. (J. H. Garcia, H. Kalimo, Y. Kamijyo and B. F. Trump, Virchows Archiv. [Zellopath.], 25, 191 (1977).

These and other studies have shown that the primary site of traumatic brain injury is in the grey matter where the process follows a pattern of insult, edema, ischemia, hypoxia, neuronal death and necrosis followed, in many instances, by irreversible coma or death. The discovery of a drug that specifically prevents the edema would obviate the sequalae.

Experimental head injury has been shown to produce a pathophysiological response primarily involving swelling of astroglial as a secondary, inhibitable process. At the molecular level, the sequence appears to be: trauma, elevation of extracellular $K^+$ and/or release of neurotransmitters, edema, hypoxia and necrosis. Astroglial swelling results directly from a $K^+$-dependent, cation-coupled, chloride transport from the extracellular into the intracellular compartment with a concomitant movement of an osmotic equivalent of water. Thus, an agent that specifically blocks chloride transport in the astroglia is expected to block the edema caused by trauma and other insults to the brain. It is also important that such chloride transport inhibitors be free or relatively free of side effects, particularly those characteristics of many chloride transport inhibitors, such as diuretic properties. Compounds of the type illustrated by Formula I exhibit the desired effects on brain edema and are relatively free of renal effects.

That this approach is valid has been demonstrated by the correlation of the in vitro astroglial edema inhibiting effects of chloride transport inhibitors with their ability to reduce the mortality of animals receiving experimental in vivo head injury. As a final proof, one compound (ethacrynic acid) which exhibited activity both in vitro and in vivo assays was effective in reducing mortality in clinical cases of head injury. These studies are described in the Journal of Medicinal Chemistry, Volume 25, page 567 (1982), which is hereby incorporated by reference.

Three major biological assays can be used to demonstrate biological activity of the compounds. The (1) in vitro cat cerebrocortical tissue slice assay, (2) the in vitro primary rat astrocyte culture assay and (3) the in vivo cat head injury assay. The first assay, the in vitro cat cerebrocortical tissue slice assay has been described by Marshall, L. F.; Shapiro, H. M.; Smith, R. W. In "Seminars in Neurological Surgery: Neural Trauma"; Popp, A. J.; Bourke, R. S.; Nelson, L. R.; Kimelberg, H, K,. Eds.; Raven Press: New York, 1979; p. 347, by Bourke, R. S.; Kimelberg, H, K.; Daze, M. A. in Brain Res. 1978, 154, 196, and by Bourke, R. S.; Kimelberg, H. K,; Nelson, L. R. in Brain Res. 1976, 105, 309. This method constitutes a rapid and accurate method of determining the intrinsic chloride inhibitory properties of the compounds of the invention in the target tissue.

The second assay method involves the in vitro primary rat astrocyte assay. The method has been described by Kimelberg, H. K.; Biddlecome, S.; Bourke, R. S. in Brain Res. 1979, 173, 111, by Kimelberg, H. K.; Bowman, C.; Biddlecome, S.; Bourke, R. S., in Brain Res. 1979, 177, 533, and by Kimelberg, H. K.; Hirata, H. in Soc. Neurosci. Abstr. 1981, 7, 698. This method is used to confirm the chloride transport inhibiting properties of the compounds in the pure target cells, the astrocytes.

The third assay method, the in vivo cat head injury assay has been described by Nelson, L. R.; Bourke, R. S.; Popp, A. J.; Cragoe, E. J., Jr.; Signorelli, A.; Foster, V. V. ; Creel, in Marshall, L. F.; Shapiro, H. M.; Smith, R. W. In "Seminars in Neurological Surgery: Neural Trauma"; Popp, A. J.; Bourke, R. S.; Nelson, L. R.; Kimelberg, H. K., Eds.; Raven Press: New York, 1979; p. 297.

This assay consists of a highly relevant brain injury in cats which is achieved by the delivery of rapid repetitive acceleration-deceleration impulses to the animal's head followed by exposure of the animals to a period of hypoxia. The experimental conditions of the assay can be adjusted so that the mortality of the control animals falls in the range of about 25 to 75%. Then, the effect of the administration of compounds of this invention in reducing the mortality over that of the control animals in concurrent experiments can be demonstrated.

Using the in vitro cat cerebrocortical tissue slice assay, described in Example 1, compounds of the present invention exhibited marked activity. This test provided the principal in vitro evaluation and consisted of a determination of concentration vs. response curve. The addition of $HCO_3^-$ to isotonic, $K^+$-rich saline-glucose incubation media is known to specifically stimulate the transport of $Cl^-$ coupled with $Na^+$ and an osmotic equivalent of water in incubating slices of mammalian cerebral cortex. Experiments have demonstrated that the tissue locus of swelling is an expanded astroglial compartment. Thus, the addition of $HCO_3^-$ to incubation media stimulated statistically significant and comparable increases in cerebrocortical tissue swelling and ion levels. After addition of drug to the incubation media, detailed drug concentration-response curves were then obtained. The data were expressed as percent $HCO_3^-$-stimulated swelling vs. drug concentration, from which the concentration of drug providing 50% inhibition of $HCO_3^-$-stimulated swelling ($I_{50}$ in molarity) was interpolated. The results are expressed in Table I, below:

TABLE I

| Enantiomer | | $I_{50}$, M |
|---|---|---|
| [(6,7-dichloro-2-cyclopentyl-2,3-dihydro-2-methyl-1-oxo-1H—inden-5-yl)amino]acetic acid | ±(racemate) | $8 \times 10^{-9}$ |
| [(6,7-dichloro-2-cyclopentyl-2,3-dihydro-2-methyl-1-oxo-1H—inden-5-yl)amino]acetic acid | + | $10^{-7}$ |
| [(6,7-dichloro-2-cyclopentyl-2,3-dihydro-2-methyl-1-oxo-1H—inden-5-yl)amino]acetic acid | − | $4 \times 10^{-9}$ |

Thus, in the in vitro assay compounds of Formula I inhibit chloride transport by 50% at concentrations as low as $4 \times 10^{-9}$ molar.

The following examples are included to illustrate the in vitro cerebrocortical tissue slice assay, the preparation of representative compounds of Formula I and representative dosage forms of these compounds. It is intended that the specification and examples be considered as exemplary only, with the true scope and spirit of the invention being indicated by the following claims.

EXAMPLE 1

In Vitro Cerebrocortical Tissue Slice Assay

Adult cats of 2–3 kg body weight were employed in tissue slice studies. Prior to sacrifice, the animals were anesthetized with ketamine hydrochloride (Ketaset), 10 mg/kg im. Eight (three control, five experimental) pial surface cerebrocortical tissue slices (0.5-mm thick; approximately 150 mg initial fresh weight) were cut successively with a calibrated Stadie-Riggs fresh tissue microtome without moistening and weighed successively on a torsion balance. During the slice preparation all operations except weighing were confined to a humid chamber. Each slice was rapidly placed in an individual Warburg flask containing 2 ml of incubation medium at room temperature. The basic composition of the incubation media, in millimoles per liter, was as follows: glucose, 10; $CaCl_2$, 1.3; $MgSO_4$, 1.2; $KH_2SO_4$, 1.2; Hepes (N-2-hydroxy-ethylpiperazine-N'-2-ethanesulfonic acid, titrated with NaOH to pH 7.4), 20. Except when adding $HCO_3^-$, the osmolarity of the media was maintained isosmotic (approximately 285 mOsm/L) by reciprocal changes of $Na^+$ or $K^+$ to achieve a concentration of $K^+$ of 27 mM. The basic medium was bubbled for 30 minutes with 100% $O_2$ before use. When added, $NaHCO_3$ or triethylammonium bicarbonate (TEAB) was initially present in the sidearm of each flask at an initial concentration of 50 mM in 0.5 ml of complete medium. Nonbicarbonate control slices were incubated at 37° C. in 2.5 ml of basic medium for 60 minutes. Bicarbonate control slices were similarly incubated for an initial 20 minutes at 37° C. in 2.0 ml of basic medium to which was added from the sidearm an additional 0.5 ml of incubation medium containing 50 mM $HCO_3^-$, which, after mixing, resulted in a $HCO_3^-$ concentration of 10 mM and a total volume of 2.5 ml. The incubation continued for an additional 40 minutes. The various compounds tested were dissolved by forming the sodium salts by treatment with a molar equivalent of $NaHCO_3$ and diluting to the appropriate concentrations. Just prior to incubation, all flasks containing $HCO_3^-$ were gassed for 5 minutes with 2.5% $CO_2/97.5\%$ $O_2$ instead of 100% $O_2$.

Following the 60-minute incubation period, tissue slices were separated from incubation medium by filtration, reweighed, and homogenized in 1N $HClO_4$ (10% w/v) for electrolyte analysis. The tissue content of ion is expressed in micromoles per gram initial preswelling fresh weight. Control slice swelling is expressed as microliters per gram initial preswelling fresh weight. The effectiveness of an inhibitor at a given concentration was measured by the amount of $HCO_3^-$-stimulated swelling that occurred in its presence, computed as a percent of the maximum possible. Tissue and media $Na^+$ and $K^+$ were determined by emission flame photometry with $Li^+$ internal standard; $Cl^-$ was determined by amperometric titration. Tissue viability during incubation was monitored by manometry.

EXAMPLE 2

Preparation of [(6,7-Dichloro-2-cyclopentyl-2,3-dihydro-2-methyl-1-oxo-1H-inden-5-yl)amino]acetic acid Step A:

5(2-Bromoethoxy)-6,7-dichloro-2-cyclopentyl-2,3-dihydro-2-methyl-1H-inden-1-one

A stirred mixture of 2,3-dichloro-2-cyclopentyl-2,3-dihydro-5-hydroxy-2-methyl-1H-inden-1-one (60 g, 0.20 mole) and postassium carbonate (55 g, 0.40 mole) in dimethylformamide (400 ml) is warmed at 60° C. for ½ hour then treated with ethylene bromide (376 g, 2.0 mole) and heated at 60° C. for 2 hours. The reaction mixture is poured into ice water (4 l) to give 37.5 g of 5(2-bromoethoxy)-6,7-dichloro-2- cyclopentyl-2,3-dihydro-2-methyl-1H-inden-1-one which melts at 124°–125° C. after recrystallization from ethanol.

Elemental Analysis for $C_{17}H_{19}BrCl_2O_2$:
Calc'd: C, 50.27; H, 4.72
Found: C, 50.13; H, 4.93

Step B:

6,7-Dichloro-2-cyclopentyl-2,3-dihydro-5-(2-hydroxyethylamino)-2-methyl-1H-inden-1-one A mixture of 5-(2-bromoethoxy)-6,7-dichloro-2-cyclopentyl-2,3-dihydro-2-methyl-1H-inden-1-one (30 g) and liquid ammonia (700 ml) are shaken in a high pressure reaction vessel for 3 days at 25° C. The ammonia is vented and the residue recrystallized from nitromethane (200 ml) to give 18.9 g of 6,7-dichloro-2-cyclopentyl-2,3-dihydro-5-(hydroxyethylamino)-2- methyl-1H-inden-1-one which melts at 135-136° C.

Elemental Analysis for $C_{17}H_{21}Cl_2NO_2$:
Calc'd: C, 59.66; H, 6.18; N, 4.09
Found: C, 59.80; H, 6.27; N, 4.16

Step C:

5-Amino-6,7-dichloro-2-cyclopentyl-2,3-dihydro-2-methyl-1H-inden-1-one

A stirred solution of 6,7-dichloro-2-cyclopentyl-2,3-dihydro-5-(2-hydroxyethylamino)-2-methyl-1H-inden-1-one (2.0 g) in acetone (50 ml) is treated with Jones Reagent (3 ml) at 25° C. over a 1 hour period. The reaction mixture is allowed to stand overnight then filtered free of chromium salts. The acetone is evaporated in vacuo and the 5-amino-6,7-dichloro-2-cyclopentyl-2,3-dihydro-2- methyl-1H-inden-1-one thus obtained (800 mg) is used in Step D without further purification.

Step D:

[(6,7-Dichloro-2-cyclopentyl-2,3-dihydro-2-methyl-1-oxo-1H-inden-5-yl)amino]acetic acid A mixture of 5-amino-6,7-dichloro-2-cyclopentyl-2,3-dihydro-2-methyl-1H-inden-1-one (800 mg), postassium carbonate (440 mg), and ethyl bromoacetate (540 mg) in acetone (20 ml) is heated at reflux overnight. The reaction mixture is filtered, the acetone is distilled at reduced pressure and the residual oil is dissolved in a mixture of ethanol (5 ml) and methylene chloride (5 ml) and treated with 10 N sodium hydroxide (2 ml). The mixture is stirred overnight, the solvents are distilled at reduced pressure and the residue is treated with water, then filtered and acidified with hydrochloric acid and extracted with ethyl acetate. Evaporation of the ethyl acetate gives 150 mg of [(6,7-dichloro-2-cyclo-pentyl-2,3-dihydro-2-methyl-1-oxo-1H-inden-5-yl)amino]acetic acid which melts at 199°-200° C. after recrystallization from chloroform-hexane.

Elemental Analysis for $C_{17}H_{19}Cl_2NO_3$:
Calc'd: C, 57.32; H, 5.38; N, 3.93
Found: C, 56.94; H, 5.62; N, 3.70

EXAMPLE 3

Preparation of the (+) Enantiomer of [(6,7-Dichloro-2-cyclopentyl-2,3-dihydro-2-methyl-1-oxo-1H-inden-5-yl)oxy]acetic acid By following substantially the procedure described in Example 2, Steps A through D, but substituting for the 2,3-dichloro-2-cyclopentyl-2,3-dihydro-5-hydroxy-2-methyl-1H-inden-1-one therein described an equimolar amount of (+)2,3-dichloro-2-cyclopentyl-2,3-dihydro-5-hydroxy-2-methyl-1H-inden-1one there is obtained (+)[6,7-dichloro-2-cyclopentyl-2,3-dihydro-2-methyl-1-oxo-1H-inden-5-yl)oxy]acetic acid monohydrate after precipitation from dilute sodium hydroxide with dilute hydrochloric acid.

Elemental Analysis for $C_{17}H_{19}Cl_2NO_3 \cdot H_2O$:
Calc'd: N, 3.74; H, 5.65; Cl, 18.95
Found: N, 3.77; H, 5.30; Cl, 18.92

EXAMPLE 4

Preparation of (−) Enantiomer of [(6,7-Dichloro-2-cyclopentyl-2,3-dihydro-2-methyl-1-oxo-1H-inden-5-yl)oxy]acetic acid By following substantially the procedure described in Example 2, Steps A through D, but substituting for the 2,3-dichloro-2-cyclopentyl-2,3-dihydro-5-hydroxy-2-methyl-1H-inden-1-one therein described an equimolar amount of (−)2,3-dichloro-2-cyclopentyl-2,3-dihydro-5-hydroxy-2-methyl-1H-inden-1one there is obtained (−)[(6,7-dichloro-2-cyclopentyl-2,3-dihydro-2-methyl-1-oxo-1H-inden-5-yl)oxy]acetic acid hemisemietherate after evaporation of an ethereal solution.

Elemental Analysis for $C_{17}H_{19}Cl_2NO_3\frac{1}{4}(C_2H_5)_2O$
Calc'd: C, 57.69; H, 5.78; N, 3.74
Found: C, 57.40; H, 5.94; N, 3.49

EXAMPLE 5

Parenteral solution of the (−)-enantiomer of [(6,7-dichloro-2-cyclopentyl-2,3-dihydro-2-methyl-1-oxo-1H-inden-5-yl)amino]acetic acid The (−)-enantiomer of [(6,7-dichloro-2-cyclopentyl-2,3-dihydro-2-methyl-1-oxo-1H-inden-5-yl) amino]acetic acid (Example 4) (500 mg) is dissolved by stirring and warming with 0.25 N sodium bicarbonate solution (5.4 ml). The solution is diluted to 10 ml and sterilized by filtration. All the water that is used in the preparation is pyrogen-free. The concentration of the active ingredient in the final solution is 5%.

Similar parenteral solutions can be prepared by replacing the active ingredient of the above example by any of the other compounds of this invention.

EXAMPLE 6

Dry-Filled Capsules Containing 100 mg of Active Ingredient Per Capsule

|  | Per Capsule |
|---|---|
| (−)-enantiomer of [(6,7-dichloro-2-cyclopentyl-2,3-dihydro-2-methyl-1-oxo-1H—inden-5-yl)amino]acetic acid | 100 mg |
| Lactose | 99 mg |
| Magnesium Stearate | 1 mg |
| Capsule (Size No. 1) | 200 mg |

The (−)-enantiomer of [(6,7-dichloro-2-cyclopentyl-2,3- dihydro-2-methyl-1-oxo-1H-inden-5-yl) amino]acetic acid (Example 4) is reduced to a No. 60 powder and then the lactose and magnesium stearate are passed through a No. 60 bolting cloth onto the powder and the combined ingredients admixed for 10 minutes and then filled into a No. 1 dry gelatin capsule.

Similar capsules can be prepared by replacing the active ingredient of the above example by any of the other compounds of this invention.

What is claimed is:

1. A compound of the formula:

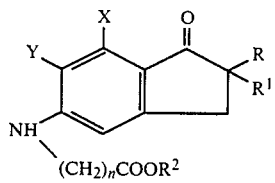

wherein
R is lower alkyl, aryl, halo substituted aryl, aralkyl, cycloalkyl or cycloalkyl-lower alkyl;
$R^1$ is hydrogen or lower alkyl;
$R^2$ is hydrogen, lower alkyl or lower alkyl-amino-lower-alkyl;
X and Y are halo or lower alkyl; and
n is 1 to 4;
or the pharmaceutically acceptable salts thereof.

2. A compound of the formula:

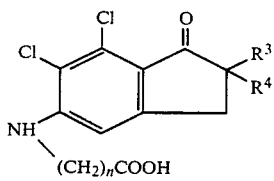

wherein
$R^3$ is aryl, halo substituted aryl or cycloalkyl;
$R^4$ is lower alkyl; and
n is 1 to 4;
or the pharmaceutically acceptable salts thereof.

3. A compound according to claim 2, wherein $R^3$ is phenyl or cyclopentyl; $R^4$ is methyl; and n is 1.

4. A compound according to claim 2, which is [(6,7-dichloro-2-cyclopentyl-2,3-dihydro-2-methyl-1-oxo-1H-inden-5-yl)amino]acetic acid.

5. A compound according to claim 4, which is the (+)-enantiomer.

6. A compound according to claim 4, which is the (−)-enantiomer.

7. A pharmaceutical composition useful in the treatment of brain injury comprising a pharmaceutical carrier and an effective amount of a compound of claim 1.

8. A pharmaceutical composition useful in the treatment of brain injury comprising a pharmaceutical carrier and an effective amount of the compound of claim 6.

9. A method of treating a person with brain injury which comprises administering to such a person an effective amount of a compound of claim 1.

10. A method according to claim 9, which comprises administering to a person with brain injury an effective amount of the compound of claim 6.

11. A method according to claim 9, which comprises administering to a person with brain injury an effective amount of the pharmaceutical composition of claim 7.

12. A method according to claim 9, which comprises administering to a person with brain injury an effective amount of the pharmaceutical composition of claim 8.

* * * * *